United States Patent [19]

Walsdorf et al.

[11] Patent Number: 5,075,499
[45] Date of Patent: Dec. 24, 1991

[54] CALCIUM SUPPLEMENTATION BY DICALCIUM CITRATE-LACTATE

[75] Inventors: Neill B. Walsdorf; George Alexandrides, both of San Antonio; Charles Y. C. Pak, Dallas, all of Tex.

[73] Assignees: Board of Regents, The University of Texas System, Austin; Mission Pharmacal Company, San Antonio, both of Tex.

[21] Appl. No.: 275,046

[22] Filed: Nov. 21, 1988

[51] Int. Cl.$^5$ .................... C07C 55/00; A61K 31/19
[52] U.S. Cl. .................................... 562/590; 514/574
[58] Field of Search ................. 514/574; 562/509, 590

[56] References Cited

FOREIGN PATENT DOCUMENTS

| 173172 | 8/1981 | Japan . |
|---|---|---|
| WO 86/04814 | 8/1986 | PCT Int'l Appl. . |
| WO 86/04815 | 8/1986 | PCT Int'l Appl. . |
| WO 87/05507 | 9/1987 | PCT Int'l Appl. . |

OTHER PUBLICATIONS

McCarron et al., Dietary Calcium in Human Hypertension, Science, vol. 217, Jul. 16, 1982, pp. 267–269.
McCarron, Low Serum Concentrations of Ionized Calcium in Patients with Hypertension, The New England Journal of Medicine, vol. 307, No. 4, Jul. 22, 1982, pp. 226–228.
Ackley et al., Dairy Products, Calcium, and Blood Pressure, The American Journal of Clinical Nutrition, vol. 38, Sep. 1983, pp. 457–461.
Belizan et al., Reduction of Blood Pressure with Calcium Supplementation in Young Adults, JAMA, vol. 249, No. 9, Mar. 4, 1983, pp. 1161–1165.
Belizan et al., Preliminary Evidence of the Effect of Calcium Supplementation on Blood Pressure in Normal Pregnant Women, Am. J. Obstet, Gynecol., vol. 146, No. 2, May 15, 1983, pp. 175–180.
Nordin et al., Treatment of Spinal Osteoporosis in Postmenopausal Women, British Medical Journal, Feb. 16, 1980, pp. 451–454.
Recker et al., Effect of Estrogens and Calcium Carbonate on Bone Loss in Postmenopausal Women, Annals of Internal Medicine, vol. 87, No. 5, Dec. 1977, pp. 649–655.
Harvey et al., Calcium Citrate: Reduced Propensity for the Crystallization of Calcium Oxalate in Urine Resulting from Induced Hypercalciuria of Calcium Supplementation, Journal of Clinical Endocrinology and Metabolism, vol. 61, No. 6, Jul. 85, pp. 1223–1225.

(List continued on next page.)

Primary Examiner—Frederick E. Waddell
Assistant Examiner—Raymond J. Henley, III
Attorney, Agent, or Firm—Arnold, White & Durkee

[57] ABSTRACT

One aspect of the present invention includes the novel compound having the formula:

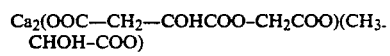

$Ca_2(OOC-CH_2-COHCOO-CH_2COO)(CH_3-CHOH-COO)$

In another aspect of the present invention, a method is provided for the treatment of a calcium related pathology. The inventive method includes the steps of providing a pharmaceutically acceptable composition, including as the active principle the compound dicalcium citrate-lactate, and administering to an individual in need thereof a therapeutically effective amount of said pharmaceutically acceptable composition.

In yet another aspect of the present invention, a process is provided for producing the compound dicalcium citrate-lactate. The inventive process comprising the steps of: (a) admixing stoichiometric quantities of citric acid and a calcium compound selected from the group consisting of calcium carbonate, calcium oxide and calcium hydroxide; (b) initiating a reaction by admixing stoichiometric quantities of lactic acid and water with said citric acid and calcium compound of step (a); (c) mixing the reactance of step (b) to produce a dense, hydrated mixture comprising calcium ions, citrate ions and lactate ions in a ratio of about 2:1:1; and (d) dehyrating the dense, hydrated mixture of step (c).

12 Claims, 2 Drawing Sheets

OTHER PUBLICATIONS

Pak, Bioavailability and Clinical Uses of Calcium Salts, CRN Quarterly, 1988, vol. 12, No. 3, pp. 8-10.

Pak et al., Enhanced Calcium Bioavailability from a Solubilized Form of Calcium Citrate, Journal of Clinical Endocrinology and Metabolism, vol. 65, No. 4, 1987, pp. 801-805.

Harvey et al., Dose Dependency of Calcium Absorption: A Comparison of Calcium Carbonate and Calcium Citrate, Journal of Bone and Mineral Research, vol. 3, No. 3, 1988, pp. 253-258.

Chem. Abstracts, 75(10):67476 (1971), Rosenthaler et al.

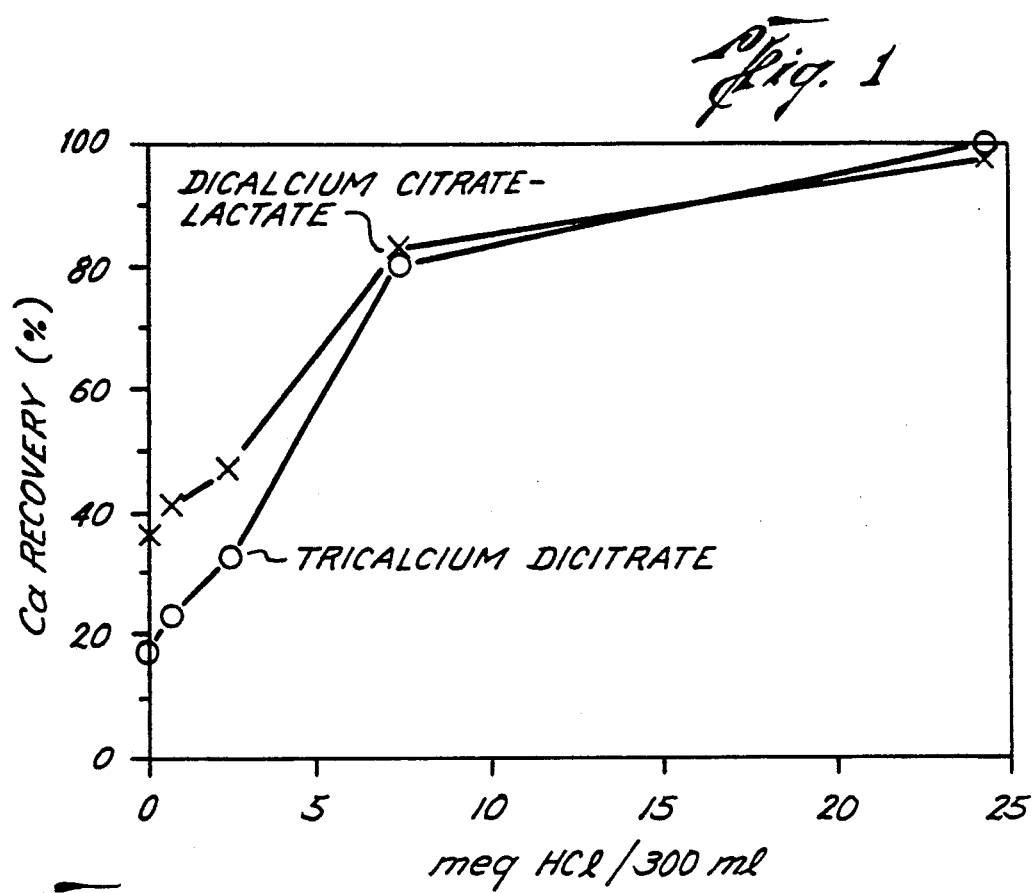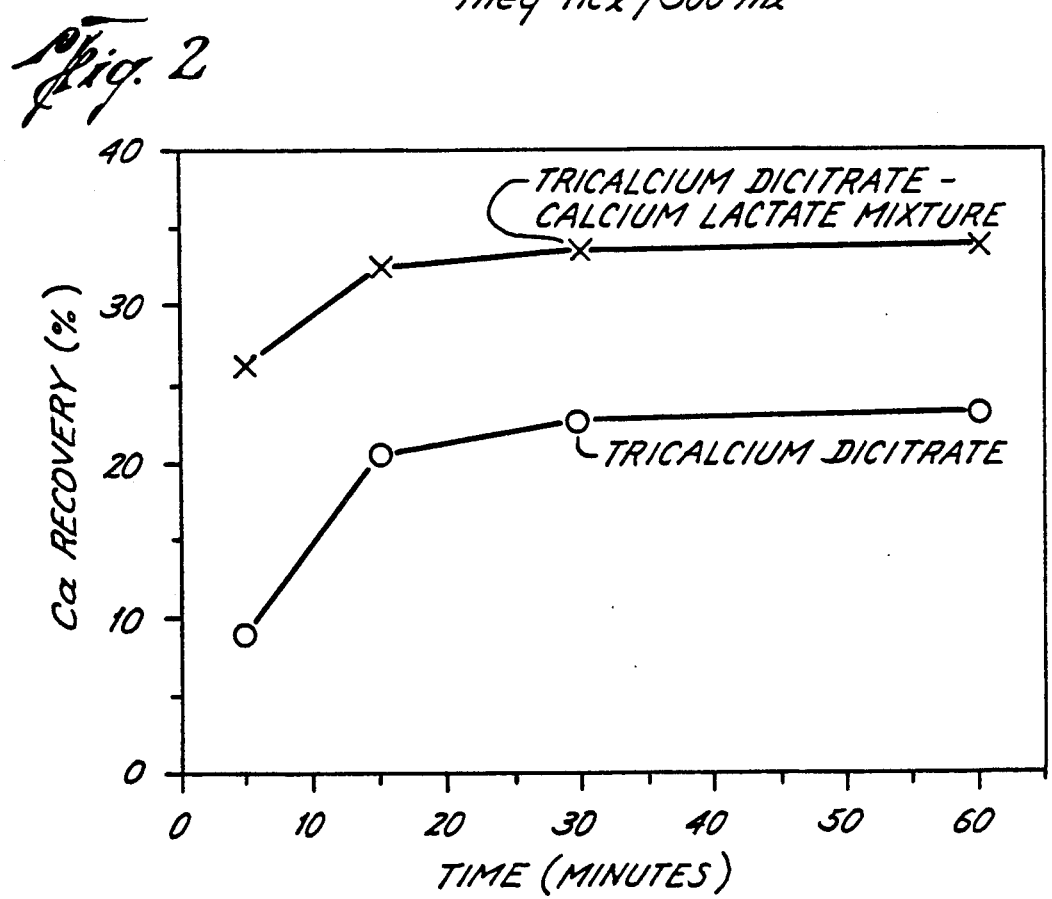

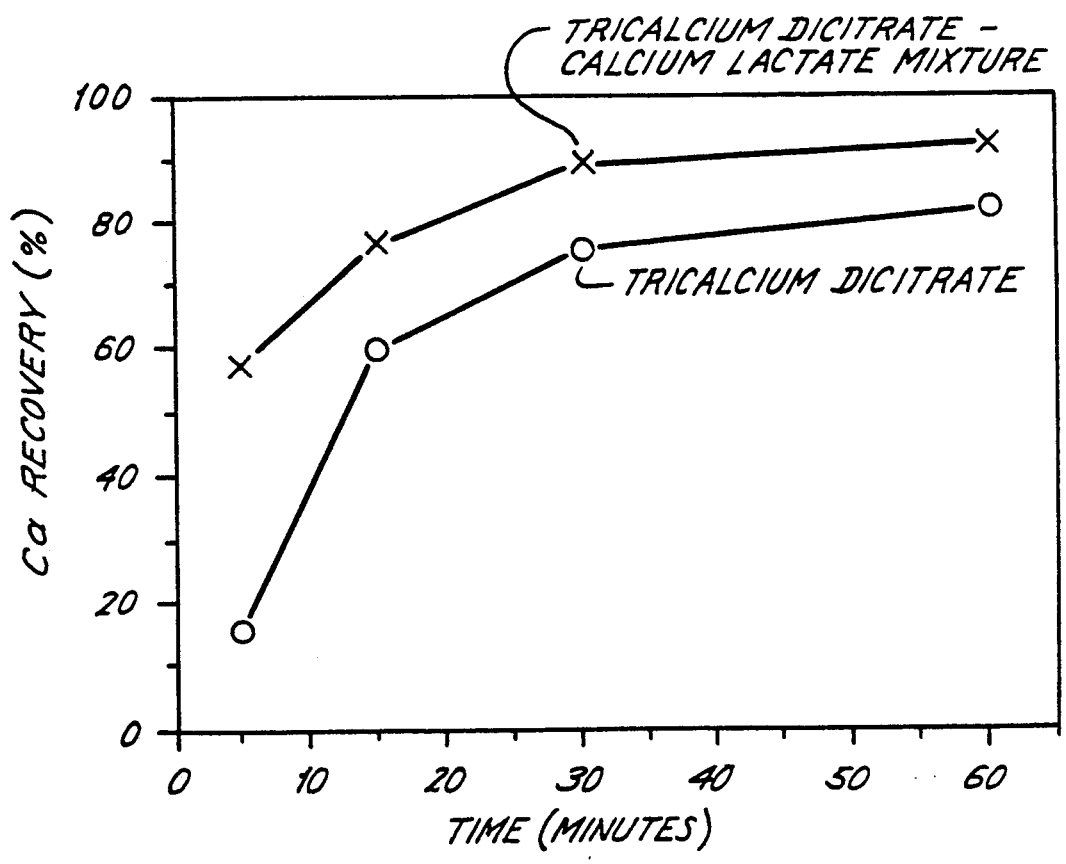

CALCIUM SUPPLEMENTATION BY DICALCIUM CITRATE-LACTATE

BACKGROUND OF THE INVENTION

Adequate calcium intake is critical for normal skeletal growth and is necessary for the prevention of osteoporosis. Often, calcium supplementation of the diet is needed to achieve this intake. Calcium is an important human dietary component. Calcium is required for adequate bone formation and maintenance, as well as for diverse metabolic functions. These diverse metabolic functions of calcium are incompletely understood but likely involve, at least in part, the alteration and functional control of proteins such as enzymes.

An assurance of adequate dietary calcium intake is thus important for normal development, metabolism and maintenance. Dietary calcium intake alone however is insufficient to assure that adequate calcium levels are available for required body functions. Dietary calcium must be absorbed from the digestive tract before it may be utilized. The intestinal absorption of calcium is enhanced by vitamin D and may also be affected by the particular chemical form of ingested calcium. Furthermore, the urinary excretion of absorbed calcium must be considered, particularly for individuals who may be subject to the formation of calcium-containing kidney stones.

Among the pathologies of particular relevance to calcium dietary requirements is osteoporosis. Osteoporosis, a condition characterized by decreases in bone mass, renders bones more fragile and susceptible to fracture. The increasingly older population of this country, since osteoporosis is usually an age-related phenomenon, further accentuates the significance of this condition. Post-menopausal women are generally agreed to be most susceptible to osteoporosis. As demonstrated by Heaney et al. (J. Lab. Clin. Med. (1978) Vol. 92 No. 6 pp. 953 to 963), postmenopausal women, unless treated with estrogens, required an increased calcium intake to maintain a zero calcium balance. This increased required intake was ascribed as due to a decrease in the production of an active vitamin D compound and calcium absorption, both perhaps related to the absence of estrogens. Recker et al. (Annals Int. Med. (1977) Vol. 87 No. 6 pp. 649 to 655) demonstrated that further bone losses in osteoporosis prone postmenopausal women may be prevented by estrogen treatment or, to a lesser extent, by dietary calcium carbonate supplementation.

In an additional study concerning osteoporosis of postmenopausal women, Nordin et al. (Brit. Med. J. (1980) Vol. 280 pp. 451 to 454) found three treatments that succeeded in lessening or abolishing further bone deterioration. These three treatments were: dietary calcium supplementation; estrogenic hormone treatment; and, treatment with estrogenic hormone plus 1-alpha hydroxy vitamin $D_3$.

Treatment of individuals with estrogenic hormones may have adverse effects, such as the stimulation of estrogen dependent tumors. Treatment of individuals with vitamin D derivatives may be inadvisable because of potentially toxic effects when excess vitamin D is administered. An effective dietary calcium supplementation appears to be an advisable treatment for osteoporosis.

The interrelation of calcium and hypertension has recently been the focus of much research. McCarron et al (Science (1982) Vol. 217 pp. 267 to 269) found that subjects with essential hypertension had a lower daily calcium intake (668±89 mg) then that of normotensive subjects. McCarron (N. Eng. J. Med. (1982) Vol. 307 pp. 226 to 228) indicated that while normotensive subjects and hypertensive subjects had similar serum levels of total calcium, the hypertensive subjects had lower serum levels of ionized calcium. Ackley et al. (Am. J. Clin. Nutr. (1983) Vol. 38 pp. 457 to 461) reported finding that hypertensive men consumed significantly less milk, a major source of dietary calcium, than did normotensive men.

Belizan et al. (J. Am. Med. Ass'n. (1983) Vol. 249 No. 9 pp. 1161 to 1165) indicated that young adults showed reduction in blood pressure when their diets were supplemented with 1 gm/day elemental calcium (calcium carbonate and calcium lactate-gluconate). A similar observation was made with pregnant women (Belizan et al. Am. J. Obstet. Gynecol (1983) Vol. 146 No. 2 pp. 175 to 180). Currently, a possibility exists that adequate calcium intake may be an important factor in control of blood pressure.

The interrelationship of calcium and chronic diarrheal syndrome has also been studied. This syndrome, where bone loss may occur, may result from surgical resection or inflammation of the digestive tract. Bone disease may occur because patients with this condition absorb calcium poorly from intestines. Thus, a calcium supplement might help prevent bone loss in these patients.

In chronic kidney disease, hyperphosphatencia (high blood phosphorus) may develop from the inability of the kidneys to eliminate phosphate. Calcium supplementation may also be useful here, by binding phosphate and preventing its absorption in the intestinal tract.

Supplementation of the diet with calcium appears to be an important step for the prevention and treatment of calcium related pathologies including osteoporosis, possibly hypertension, and bone loss in chronic diarrheal syndrome, and phosphate accumulation in chronic renal failure. Ideally, to be most effective, a calcium supplement should satisfy the following criteria: (1) it should dissolve readily in the gastric juice so that it can eventually be absorbed in the more distal part of the bowel; (2) it should not precipitate out of duodenal juice when the juice is alkalinized by pancreatic bicarbonate secretions; (3) it should not be "complexed" extensively by negatively charged substances in the upper part of the small bowel, a process that could reduce the amount of absorbable ionic calcium; (4) it should not have as one of its side effects the formation of kidney stones; and (5) it should be in a tablet form which can be easily swallowed without adverse gastrointestinal symptoms.

Some calcium supplements, such as tricalcium dicitrate, satisfy some of the above criteria. Tricalcium dicitrate was found to be more soluble in gastric juice than calcium carbonate, the most widely used calcium salt (Pak, CRN Quarterly, 12:8-10, 1988). Moreover, tricalcium dicitrate did not precipitate out of simulated duodenal juice (Pak, et al., J. Clin. Endoc. Metab., 65:801-805, 1987). The development of ultradense tableting technology allowed tricalcium dicitrate to be manufactured as a small, easily swallowed tablet. Tricalcium dicitrate also increased urinary citrate, which decreases the likelihood of kidney stone formation (Harvey, Zobitz and Pak, *J. Clin. Endoc. Metab.,* 61:1223-1225, 1985).

Because of their high aqueous solubility it was believed that calcium lactate or calcium gluconate would present advantages over tricalcium dicitrate supplementation. However, the calcium content for these salts is low, being 13% and 9%, respectively. Thus, to deliver a therapeutically effective amount of calcium (0.2 grams to 2.0 grams/day), in a tablet form would require an unacceptably large tablet. Moreover, these salts are not as effective as tricalcium dicitrate in raising urinary citrate. Accordingly, these salts do not as effectively decrease the likelihood of calcium-containing kidney stone formation that could occur from calcium supplementation.

However, even a calcium supplement as effective as tricalcium dicitrate does not satisfy all of the criteria for an ideal supplement. Tricalcium dicitrate preparations, for example, may not dissolve completely, under certain conditions, in states of basal or low gastric acid secretion. Furthermore, large amounts of solubilized calcium become complexed to citrate in the proximal bowel where a substantial portion of calcium is absorbed. It is believed that ionic calcium is better absorbed (bioavailable) than complexed calcium. Thus, formation of a soluble calcium-citrate complex could lower the amount of calcium absorbed by reducing the total ionic calcium pool.

Dietary calcium supplementation is generally considered an effective method for preventing or treating a calcium deficiency or pathology related to such deficiency. However, typical available dietary calcium supplements are often plagued by the problems of poor absorption, low calcium content, poor solubility in gastric juice, and insufficient bioavailability of solubilized calcium. Thus, a new calcium supplement which effectively overcomes these problems is needed. The dietary calcium supplement of the present invention provides an answer to such needs.

SUMMARY OF THE INVENTION

The present invention involves methods and compositions for efficient dietary calcium supplementation. The compositions involve calcium in the presence of citric acid and lactic acid or their salts, most preferably these are combined as calcium salts of these acids, individually or in combination.

A most preferred calcium salt for dietary calcium supplementation is a dicalcium citrate-lactate consisting of two calcium ions one citrate ion and one lactate ion (2:1:1). This dicalcium citrate-lactate is a compound having the representative formula:

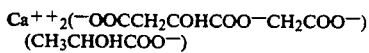

and has an anhydrous molecular weight of about 358.2 and a calcium content of about 22.4% by weight.

An important aspect of the present invention is a method for the treatment or prevention of a pathology related to calcium deficiency of an individual. This method comprises generally providing unit dosage forms of calcium suitable for dietary supplementation which consist essentially of calcium ion, citrate ion and lactate ion in a most preferred molar ratio of about 2:1:1. When such a unit dosage form is enterally administered to an individual, preferably on a daily basis, calcium is efficiently absorbed and any deficiency remedied.

The most preferred method of preventing calcium deficiencies or remedying pathological conditions in an individual resulting from such deficiencies involves:(a) providing a pharmaceutically acceptable composition including as an active principle the compound dicalcium citrate-lactate having the formula

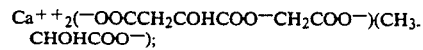

and (b) administering to the individual a therapeutically effective amount of said pharmaceutically acceptable composition. This therapeutically effective amount is most preferably in a tablet form for ease of administration.

The preferred tablet form usually includes at least one of a pharmaceutically acceptable binder, diluent, cipient, carrier, lubricant, coloring agent, and flavoring agent. A therapeutically effective amount includes from about 0.2 gram to about 2.0 grams of calcium/day.

The most preferred method of the present invention for the treatment or prevention of a pathology related to calcium deficiency in an individual, more specifically includes the steps of: (a) providing a pharmaceutically acceptable tablet, including as the active principle from about 50 to about 99.9% by weight of the compound

and (b) administering (probably on a daily basis) to the individual a therapeutically effective amount of said pharmaceutically acceptable tablet comprising from about 0.2 gram to about 2.0 (more preferably 0.5 gram) gram of calcium.

The present invention also provides a less preferred but still effective method for the treatment or prevention of a pathology related to calcium deficiency in an individual. This less preferred method comprises the steps of: (a) providing a pharmaceutically acceptable composition including as active principles, tricalcium dicitrate and calcium lactate in a molar ratio between about 1:1 and about 2:1; and (b) administering to the individual a therapeutically effective amount of said pharmaceutically acceptable composition. The most preferred molar ratio of tricalcium dicitrate to calcium lactate is about 1.73:1.

The methods of remedying calcium deficiency as related to the present invention generally involve an inadequate dietary calcium intake on the part of the individual suffering said deficiency. The provision of and use of a dietary supplement comprising calcium, citrate or citric acid, and lactate or lactic acid is a general teaching of the present invention. The pathology of greatest potential for prevention or treatment is osteoporosis although it may also be hypertension, bone loss in chronic diarrheal syndrome or any other condition for which an increased intake of dietary calcium is beneficial.

A preferred process for producing a compound having the formula:

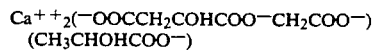

and being in a form suitable for tableting has been devised and is a component of the present invention. This preferred process comprising the steps of:

(a) mixing amounts of citric acid and a calcium compound selected from the group consisting of calcium carbonate, calcium oxide, and calcium hydroxide in a 1:2 molar ratio to form a first mixture; (It is understood that minor variations may be made in the molars ratios of citric acid and calcium compound to result in essentially the same result.)

(b) adding to the first mixture an amount of lactic acid about equimolar to the amount of citric acid, and water, to form a second mixture comprising between about 25 weight percent water and about 40 weight percent water;

(c) blending the second mixture to produce a dense, hydrated mixture comprising calcium ions, citrate ions, and lactate ions in a molar ratio of 2:1:1; (It is understood that minor variations in this ratio may occur resulting in an essentially similar composition) and (d) drying and milling said dense, hydrated mixture to produce a granulated composition comprising up to about 10 weight percent water and having a bulk density greater than about 0.7 g/cc, said composition being suitable for tableting. The granulated composition has a prefered bulk density greater than about 1.0 g/cc. The most preferred calcium compound is calcium oxide although calcium carbonate allows certain process advantages. The water added in step (b) is most preferably at a temperature greater than about 60° C.

BRIEF DESCRIPTION OF THE DRAWINGS

FIG. 1 illustrates the solubility of dicalcium citrate-lactate (X) and tricalcium dicitrate (O) after one hour in various aqueous hydrochloric acid solutions.

FIG. 2 shows calcium solubility from tricalcium dicitrate (o) and a tricalcium dicitrate-calcium lactate mixture (x), both in 0.72 meq HCl/300 ml water.

FIG. 3 shows calcium solubility from tricalcium dicitrate (o) and a tricalcium dicitrate-calcium lactate mixture (x), both in 7.26 meq HCl/300 ml water.

DESCRIPTION OF THE PREFERRED EMBODIMENTS

This invention generally relates to methods for producing and utilizing a novel compound, dicalcium citrate-lactate, having the empirical formula:

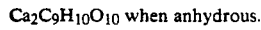

$Ca_2C_9H_{10}O_{10}$ when anhydrous.

It has been demonstrated that dicalcium citrate-lactate comprises a crystalline structure of calcium: citrate: lactate in a molar ratio of 2:1:1. Dicalcium citrate-lactate has a molecular weight of about 358.2 and a calcium content of about 22.4%. Dicalcium citrate-lactate may be illustrated by the likely symbolic structural formula:

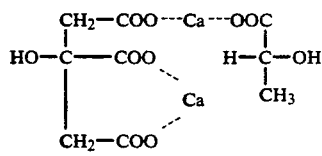

One aspect of the invention is directed to a method for the treatment of a calcium related pathology. This inventive method includes the steps of: (a) providing a pharmaceutically acceptable composition, including as the active principle the novel compound dicalcium citrate-lactate; and (b) administering to an individual in need thereof a therapeutically effective amount of said pharmaceutically acceptable composition.

The first step in the inventive method is providing a pharmaceutically acceptable composition. In the most preferred embodiment the pharmaceutically acceptable composition is a tablet for ingestion. According to a preferred embodiment this tablet includes, as the active principle, from about 50 to 99.9% by weight dicalcium citrate-lactate and at least one pharmaceutically acceptable substance. In the most preferred embodiment, this tablet contains more than 75% by weight dicalcium citrate-lactate and at least one substance selected from the group consisting of pharmaceutically acceptable binders, diluents, excipients, carriers, lubricants, coloring agents, and flavoring agents.

Tablets of dicalcium citrate-lactate, prepared according to a preferred embodiment, possess superior bioavailability as compared to other calcium supplements. It is demonstrated herein that calcium absorption, for example, is significantly greater from dicalcium citrate-lactate tablets than from tricalcium dicitrate tablets. Healthy volunteers were administered dicalcium citrate-lactate tablets and tricalcium dicitrate tablets, each containing 400 mg of elemental calcium. Calcium absorption was measured from the increment in urinary calcium during the second two hours following the administration of the oral calcium tablets. Calcium absorption from the dicalcium citrate-lactate tablets was determined to be greater than that of calcium absorption from tricalcium dicitrate tablets.

It is also demonstrated herein that dicalcium citrate-lactate tablets, prepared according to a preferred embodiment, are more soluble in simulated gastric juices than several other prior art calcium supplement tablets, for example, tricalcium dicitrate tablets. The solubility of dicalcium citrate-lactate and tricalcium dicitrate tablets, each containing 400 milligrams of elemental calcium, in varying amounts of hydrochloric acid to mimic different levels of gastric acid secretion in human beings was studied. The solubility of dicalcium citrate-lactate tablets was determined to be greater than that of tricalcium dicitrate tablets in solutions of hydrochloric acid content of less than 7.6 meq/300 ml, that is, in states of basal or impaired gastric acid secretion.

Tablets of dicalcium citrate-lactate, prepared according to a preferred embodiment, also have a higher calcium content than other acceptable water-soluble calcium supplements, for example, calcium gluconate and calcium lactate. Calcium gluconate and calcium lactate contain 9% and 13% calcium respectively, while dicalcium citrate-lactate contains about 22.4%. Accordingly, a therapeutically effective amount of calcium may be administered to a patient in need thereof in a relatively small tablet of dicalcium citrate-lactate. Because tablet size is an important factor to encourage patient compliance, the relatively diminutive tablets of this invention should increase patient compliance and facilitate the prevention and treatment of calcium related pathologies.

Another step in the present inventive method is administering to an individual in need thereof a therapeutically effective amount of said pharmaceutically acceptable composition. As set forth above, in the most preferred embodiment, the pharmaceutically acceptable composition is an oral tablet. Preferably this tablet comprises from 0.2 gram to 0.5 gram of calcium. In the most preferred embodiment the therapeutically effective amount of said pharmaceutically acceptable composition is determined by an individual's physician as that amount of calcium required to treat that individual's particular calcium related pathology. The therapeutically effective amount can be administered as a single or divided dose.

The inventive methods of the present invention are directed toward treating a calcium related pathology. In one embodiment, the calcium related pathology is osteoporosis. In another embodiment the calcium related pathology is hypertension. In still another embodiment the calcium related pathology is bone loss from a chronic diarrheal syndrome. In another embodiment the calcium related pathology is a dietary calcium deficiency. In yet another embodiment the calcium related pathology is phosphate accumulation of chronic renal disease. In general the calcium-related pathology is a pathological condition for which an increased dietary intake of calcium is beneficial.

Another aspect of the present invention is a process for producing the novel compound, dicalcium citrate-lactate. The inventive process, in one embodiment, includes the steps of: (a) mixing stoichiometric quantities of citric acid and one or more of a calcium compound selected from the group consisting of calcium carbonate, calcium oxide and calcium hydroxide; (b) initiating a reaction by admixing stoichiometric quantities of lactic acid and water with said citric acid and calcium compound of step (a); (c) mixing the reactants of step (b) to produce a dense, hydrated mixture comprising calcium ions, citrate ions, and lactate ions in ratio of about 2:1:1; and (d) dehydrating said dense hydrated mixture of step (c).

In general, the novel compound dicalcium citrate-lactate is synthesized by reacting stoichiometric quantities of citric acid, lactic acid and a calcium compound, preferably as indicated by the following reaction:

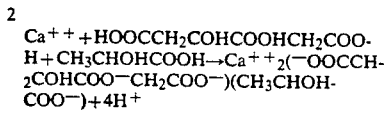

$$2Ca^{++} + HOOCCH_2COHCOOHCH_2COO^- H + CH_3CHOHCOOH \rightarrow Ca^{++}{}_2(^-OOCCH_2COHCOO^-CH_2COO^-)(CH_3CHOHCOO^-) + 4H^+$$

According to a preferred embodiment of the present inventive process, the citric acid is mixed with the calcium compound during continuous agitation. The calcium compound is one or more selected from the group consisting of calcium carbonate, calcium oxide and calcium hydroxide. Calcium oxide is the most preferred calcium compound from a cost standpoint, although the use of calcium carbonate provides better control over the temperature of the reaction mixture. Lactic acid and water are thereafter sequentially mixed, to produce a dense, hydrated mixture. The lactic acid is preferably aqueous 50 weight percent lactic acid and the water preferably is at a temperature of about 60° C. This dense hydrated mixture may be characterized as being a thick "slush" comprising calcium ions, citrate ions and lactate ions in a proportion of about 2:1:1.

The hydrated mixture preferably has a moisture content between about 25 weight percent and about 40 weight percent. This is preferable because if the moisture content falls below about 25 weight percent, it is likely that the reaction will be incomplete. Above about 40 weight percent, the mixture retains a paste-like consistency for a longer period of time, which is economically disadvantageous.

This hydrated mixture is thereafter preferably blended in a ribbon mixer to a granular mass consisting of granules and lumps. This mass is then dried and milled to produce a dicalcium citrate-lactate composition. This composition preferably has a maximum particle size of about ⅛ inch (0.3 centimeters) in diameter and a moisture content ranging up to about 10 weight percent. According to a preferred embodiment of the invention, the dicalcium citrate-lactate composition produced has a bulk density (weight per gross volume) ranging from about 0.7 g/cc to about 1.2 g/cc, and most preferably, greater than about 1.0 g/cc. Milling and sizing this bulk material produces a granular pharmaceutical material suitable for tableting.

This bulk dicalcium citrate-lactate composition is a preferred precursor for the production of dicalcium citratelactate tablets as it represents a densified source of calcium and citrate which is directly compressible. In one embodiment, a tableting composition is formed by subjoining and blending the bulk material with a lubricant such as magnesium stearate The dicalcium citrate-lactate tablets formed after tableting preferably comprise about 22 weight percent calcium, 53 weight percent citrate, and have a calcium:citrate:lactate molar ratio of about 2:1:1. Multiple station tablet presses such as a Colton #216-16 station press; a Vector #247-41 station press; or a Manesty rotopress-37 station press, for example, may be used to produce the tablets of the present invention. The dicalcium citrate-lactate tablets of the present invention are a potent delivery system. In a preferred embodiment, 10.0 meq of calcium (200 milligrams), and 7.5 meq of citrate (472 milligrams) are incorporated in each 10.0 meq tablet of dicalcium citrate-lactate (894 milligrams). The tablets thus obtained may be final products or may be further processed. Further processing to physically and aesthetically improve these tablets may be accomplished by tablet-coating procedures well known to those skilled in relevant pharmaceutical arts.

The following examples are presented to describe preferred embodiments and utilities of the present invention and are not meant to limit the present invention unless otherwise stated in the claims appended hereto.

EXAMPLE 1

Small Batch Preparation of Calcium Citrate-Lactate Compound For Tableting 38.4 grams of citric acid powder and 40 grams of calcium carbonate were thoroughly mixed in a large beaker. 36 grams of lactic acid, 50 weight percent solution, was slowly added with rapid stirring. 40 grams of water was then introduced slowly in small portions, each portion was added after the $CO_2$ evolution slowed or ceased. After drying, the material was sized and found to have a bulk density greater than 1.1 g/cc. Bulk density was determined by an Archimedean method. This dense granular dicalcium citrate-lactate was subjected to compression tableting to form tablets containing 10 meq (200 milligrams) of calcium, and 7.5 meq (472 milligrams) of citrate, with a size of 0.29 (7.47 millimeters) inch by 0.74 (1.9 centimeters) inch.

EXAMPLE 2

Large Batch Preparation Of Calcium Citrate-Lactate Compound For Tableting

The dicalcium citrate-lactate tablets of the present invention were also produced on a large scale. 38.4 kilograms of citric acid powder and calcium carbonate were placed in a Colton 7 cubic ft. ribbon mixer and blended for 2 minutes. Thirty six kilograms of the lactic acid, 50 weight percent solution, were added in approximately three equal portions, 3 minutes apart with continuous mixing. Water (40 kilograms) was added in approximately four equal portions 2-3 minutes apart with continuous mixing. Mixing continued for 10 minutes. The resultant granular and lumpy material was passed through a Fitzmill, knives forward, with no screen, trayed and dried at 212° F.–221° F. (100° C.–105° C.) for three hours. The dried product was sized and its bulk density was determined to be greater than 1.1 g/cc. The sizing was done using a Fitzmill Model No. 6 with a 31262AA screen.

The dried dicalcium citrate-lactate composition was subjoined with 1.0 weight percent magnesium stearate. The tableting composition was then tableted in a multiple station tablet press to form dicalcium citrate-lactate tablets comprising about 200 mg of calcium, about 472 mg of citrate and about 222 mg lactate.

EXAMPLE 3

Large Batch Preparation Of Calcium Citrate-Lactate Compound For Tableting

The procedure previously described in Example 2 was followed with the exception of calcium carbonate being replaced by calcium oxide. Dicalcium citrate-lactate having a bulk density of greater than 0.7 g/cc was produced.

EXAMPLE 4

Large Batch Preparation Of Calcium Citrate-Lactate Compound For Tableting

The procedure previously described in Example 2 was followed with the exception of calcium carbonate being replaced by calcium hydroxide. Calcium citrate lactate having a bulk density of greater than 0.8 g/cc was produced.

EXAMPLE 5

Bioavailability of dicalcium citrate-lactate

Ten normal volunteers underwent calcium absorption tests from ingested dicalcium citrate-lactate tablets (prepared according to Example 2) and from tricalcium dicitrate tablets, each containing 400 mg of elemental calcium. The calcium absorption was measured from the increment in urinary calcium during the second two hours following oral calcium load, expressed as mg calcium/dl glomerular filtrate (GF).

The calcium absorption from the dicalcium citrate-lactate compound was $0.084 \pm 0.049$ SD mg/dl GF, which was 91% greater than that found with tricalcium dicitrate ($0.044 \pm 0.051$ mg/dl GF).

EXAMPLE 6

Solubility Of dicalcium citrate-lactate

The solubility of dicalcium citrate-lactate, as prepared by the method described in Example 2, was determined in 300 ml of water containing varying amounts of hydrochloric acid (HCl) to mimic different levels of gastric acid secretion in human beings. The amounts of calcium compound dissolved at one hour are shown in FIG. 1. The results were compared with the solubility of tricalcium dicitrate (400 mg elemental calcium).

The solubility of dicalcium citrate-lactate was much higher than that of tricalcium dicitrate in solutions with HCl content of less than 7.6 meq/300 mg, that is, in states of basal or impaired gastric acid secretion.

EXAMPLE 7

X-ray Diffraction Analysis of Dicalcium Citrate-lactate

A sample of dicalcium citrate-lactate was prepared by the method described in Example 2 for x-ray diffraction analysis. A comparison was made with an equimolar mixture of calcium citrate and calcium lactate. The samples were lightly ground in an agate mortar and pestle to create a uniform powder. The samples were exposed to continuous x-ray exposure on a Rigaku high brilliance rotating anode x-ray generator using a copper target x-ray source, running at 50 kV and 150 mA at room temperature. The x-ray diffraction films were recorded in a germanium crystal monochromated powder diffraction camera of the Guinier design (Huber Instruments, West Germany). The samples were continuously rotated during the x-ray exposure to ensure a totally randomized sample orientation, thereby avoiding any preferred orientation which could yield spurious diffraction lines. The x-ray diffraction maxima were measured on a film reader which had an accuracy of 0.005 mm.

The x-ray diffraction pattern for the calcium citrate and calcium lactate mixture contained the diffraction maxima for calcium citrate tetrahydrate (JCPDS#28.2003), and for calcium lactate pentahydrate (JCPDS#29-1596). There were, however, some extra very weak diffraction maxima which were not accounted for in the standard patterns of the Joint Commission on Powder Defraction Standards.

The X-ray diffraction pattern for dicalcium citrate-lactate included lines for the calcium citrate tetrahydrate and calcium lactate tetrahydrate as well as a significant number of extra lines which could not be accounted for by either of those two standard patterns. Because the specific crystal structure was not known for dicalcium citrate-lactate, it was not possible to calculate the diffraction pattern for this compound, but the positions of the x-ray diffraction maxima (d-spacing in Angstroms) would suggest there is an admixture of the calcium citrate and lactate into one crystal structure.

EXAMPLE 8

Improved Solubility of A Mixture of Tricalcium Dicitrate and Calcium Lactate

A mixture of tricalcium dicitrate and calcium lactate (1.73:1 molar ratio) was prepared by combining 1.6 g of tricalcium dicitrate tetrahydrate with 0.5 g of calcium lactate pentahydrate, yielding 400 mg elemental calcium. This mixture was added to 300 ml water containing 0.72 meq hydrochloric acid, mimicking low basal gastric acid secretion of an average normal woman. While the preparation was stirred constantly at 37° C., filtrate samples were obtained at 5, 15, 30 and 60 minutes for calcium analysis. The calcium content of the filtrate represented calcium recovery or solubility of the mixture. A similar experiment was performed with tricalcium dicitrate alone containing 400 mg calcium.

At steady state (60 min), 33% of tricalcium dicitrate-calcium lactate mixture underwent dissolution, whereas only 23% of tricalcium dicitrate did (FIG. 2).

The same mixture was added to 300 ml water containing 7.26 meq hydrochloric acid (simulating low peak gastric acid secretion). The solubility of tricalcium dicitrate alone of same calcium content (400 mg) was also determined. At 60 minutes, 92% of calcium from the mixture was recovered from solution, compared to 82% for the pure tricalcium dicitrate (FIG. 3).

Thus, the aqueous solubility of tricalcium dicitrate is substantially enhanced by mixing it with calcium lactate. This increased calcium solubility should relate directly to increased bioavailability in vivo.

EXAMPLE 9

Improved Gastrointestinal Absorbability of the Mixture of Tricalcium Dicitrate and Calcium Lactate In 11 normal subjects, intestinal calcium absorption was determined from the tricalcium dicitrate-calcium lactate mixture of composition described in Example 1 and from tricalcium dicitrate. The increment in urinary calcium following oral administration of one of above substances (containing 400 mg calcium) gave an indirect measure of intestinal calcium (Harvey, Zobitz and Pak, J. Bone Min. Res., 3:253-258, 1988).

The urinary calcium during the second two hours following oral load of 400 mg calcium as tricalcium dicitrate-calcium lactate mixture was 43.8% greater than that obtained with 400 mg as tricalcium dicitrate. Thus, adding calcium lactate to tricalcium dicitrate enhanced the absorbability of calcium.

Changes may be made in particular chemical components described herein or in the steps or the sequence of steps of the methods described herein without departing from the concept and scope of the invention as defined in the following claims.

What is claimed is:

1. A compound having the formula:

Ca$^{++}{}_2$($^-$OOCCH$_2$COHCOO$^-$CH$_2$COO$^-$)(CH$_3$CHOHCOO$^-$).

2. The compound of claim 1 wherein said compound comprises calcium, citrate and lactate in a ratio of about 2:1:1.

3. The compound of claim 1 defined further as having an anhydrous molecular weight of about 358.2.

4. The compound of claim 1 defined further as being anhydrous and as having a calcium content of about 22.4% by weight.

5. A process for producing a compound having the formula Ca$^{++}{}_2$($^-$OOCCH$_2$COHCOO$^-$CH$_2$COO$^-$)(CH$_3$CHOHCOO$^-$) and being in a form suitable for tableting, the process comprising the steps of:

(a) mixing amounts of citric acid and one or more of a calcium compound selected from the group consisting of calcium carbonate, calcium oxide, and calcium hydroxide in about a 1:2 molar ratio to form a first mixture;

(b) adding to the first mixture lactic acid in an amount about equimolar to the amount of citric acid, and water, to form a second mixture comprising between about 25 weight percent water and about 40 weight percent water;

(c) blending the second mixture to produce a dense, hydrated mixture comprising calcium ions, citrate ions, and lactate ions in a molar ratio of about 2:1:1; and (d) drying and milling said dense, hydrated mixture to produce a granulated composition comprising up to about 10 weight percent water and having a bulk density greater than about 0.7 g/cc, said composition being suitable for tableting.

6. The method of claim 5 wherein the calcium compound is calcium oxide.

7. The method of claim 5 wherein the calcium compound is calcium carbonate.

8. The method of claim 5 wherein the granulated composition has a bulk density greater than about 1.0 g/cc.

9. The method of claim 5 wherein the water is at a temperature greater than about 60° C.

10. A pharmaceutically acceptable composition comprising an amount of a compound having the formula Ca$^{++}{}_2$($^-$OOCCH$_2$COHCOO$^-$CH$_2$COO$^-$)(CH$_3$CHOHCOO$^-$) and being suitable for daily nutritional calcium supplementation.

11. A tablet comprising a compound having the formula:

Ca$^{++}{}_2$($^-$OOCCH$_2$COHCOO$^-$CH$_2$COO$^-$)(CH$_3$CHOHCOO$^-$).

12. The tablet of claim 11 defined further as being from about 50 to about 99.9% by weight of the compound.

* * * * *